(12) United States Patent
Milpied et al.

(10) Patent No.: US 11,027,134 B2
(45) Date of Patent: Jun. 8, 2021

(54) ACTIVE IMPLANTABLE MEDICAL DEVICE SUCH AS A CARDIAC RESYNCHRONISER WITH DYNAMIC ADAPTATION OF AN ATRIOVENTRICULAR DELAY DEPENDING ON A DETECTED AND QUANTIFIED DEGREE OF FUSION

(71) Applicant: SORIN CRM SAS, Clamart (FR)

(72) Inventors: Paola Milpied, Paris (FR); Delphine Feuerstein, Issy les Moulineaux (FR)

(73) Assignee: Sorin CRM SAS, Clamart (FR)

( * ) Notice: Subject to any disclaimer, the term of this patent is extended or adjusted under 35 U.S.C. 154(b) by 321 days.

(21) Appl. No.: 16/062,612

(22) PCT Filed: Dec. 14, 2016

(86) PCT No.: PCT/EP2016/080880
§ 371 (c)(1),
(2) Date: Jun. 14, 2018

(87) PCT Pub. No.: WO2017/102780
PCT Pub. Date: Jun. 22, 2017

(65) Prior Publication Data
US 2019/0076654 A1    Mar. 14, 2019

(30) Foreign Application Priority Data

Dec. 18, 2015 (FR) ...................................... 1562739

(51) Int. Cl.
*A61N 1/368* (2006.01)
*A61N 1/37* (2006.01)
*A61N 1/362* (2006.01)

(52) U.S. Cl.
CPC ......... *A61N 1/3682* (2013.01); *A61N 1/3684* (2013.01); *A61N 1/36842* (2017.08);
(Continued)

(58) Field of Classification Search
CPC .... A61N 1/368; A61N 1/3682; A61N 1/3684; A61N 1/36842; A61N 1/36843;
(Continued)

(56) References Cited

U.S. PATENT DOCUMENTS 6,832,112 B1    12/2004  Bornzin
2006/0155338 A1*  7/2006  Mongeon ............. A61N 1/3627
                                                                607/9
(Continued)

FOREIGN PATENT DOCUMENTS

CN    1662278 A    8/2005
CN    1703257 A    11/2005
(Continued)

OTHER PUBLICATIONS

International Search Report and Written Opinion on International Patent Application No. PCT/EP2016/080880 dated Jun. 22, 2017. 10 pages.

(Continued)

*Primary Examiner* — Aaron F Roane
(74) *Attorney, Agent, or Firm* — Foley & Lardner LLP

(57) ABSTRACT

This disclosure relates to an active implantable medical device of the cardiac resynchronizer type. The device includes a pulse generator to produce pacing pulses, at least one detection electrode for detecting atrial and ventricular events, at least one stimulation electrode, a memory storing executable instructions, and a processor configured to execute the instructions. The processor is configured to execute the instructions to apply an atrioventricular delay (AVD) between a sensed or stimulated atrial event and the delivery of a ventricular pacing pulse, quantify a degree of fusion between the delivery of a pacing pulse to a cavity and a spontaneous contraction of another cavity, calculate a fusion rate, and modify the value of the AVD applied to the (Continued)

delivery of said ventricular pacing pulse, as a function of a comparison.

11 Claims, 10 Drawing Sheets

(52) U.S. Cl.
CPC .......... *A61N 1/3712* (2013.01); *A61N 1/3627* (2013.01); *A61N 1/36843* (2017.08)

(58) Field of Classification Search
CPC .... A61N 1/3686; A61N 1/3688; A61N 1/371; A61N 1/3708; A61N 1/3712; A61N 1/3714; A61N 1/3716; A61N 1/362; A61N 1/3621; A61N 1/3622; A61N 1/3624; A61N 1/3625; A61N 1/3627; A61N 1/3628
USPC ............................................................ 607/9
See application file for complete search history.

(56) References Cited

U.S. PATENT DOCUMENTS

| | | | |
|---|---|---|---|
| 2009/0299423 A1* | 12/2009 | Min | A61N 1/368 607/9 |
| 2010/0069988 A1 | 3/2010 | Ding et al. | |
| 2013/0197599 A1* | 8/2013 | Sambelashvili | A61N 1/36514 607/25 |
| 2015/0246235 A1* | 9/2015 | Ghosh | A61N 1/3712 607/28 |

FOREIGN PATENT DOCUMENTS

| | | |
|---|---|---|
| CN | 103796714 A | 5/2014 |
| CN | 105120944 A | 12/2015 |
| EP | 1 205 214 A1 | 5/2002 |
| EP | 1 905 480 A1 | 4/2008 |
| EP | 2 311 524 A1 | 4/2011 |
| EP | 2 324 885 A1 | 5/2011 |
| EP | 2 742 971 A1 | 6/2014 |
| EP | 2 742 973 A1 | 6/2014 |
| EP | 2 756 865 A1 | 7/2014 |
| EP | 2 803 385 A1 | 11/2014 |

OTHER PUBLICATIONS

First Office Action issued in Chinese Application No. 201680074246.0 dated Jan. 22, 2021.

* cited by examiner

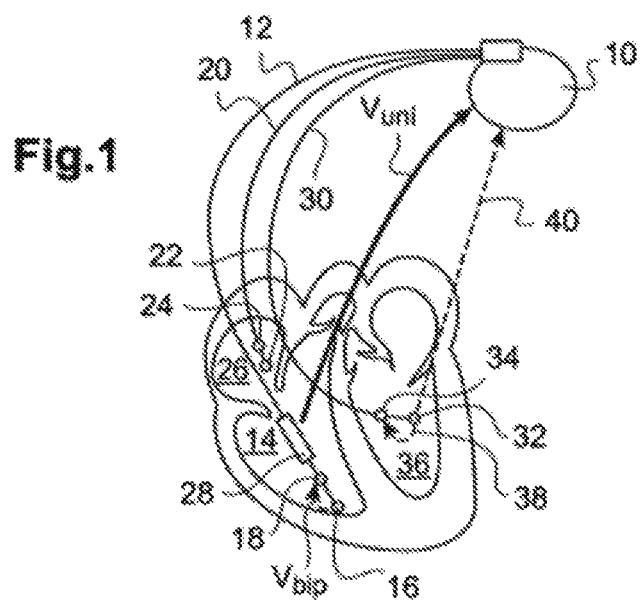

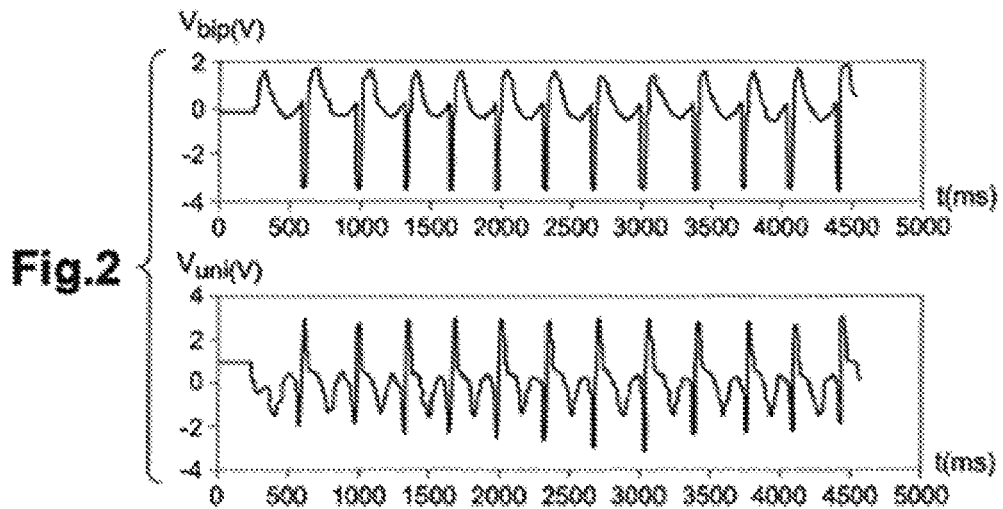
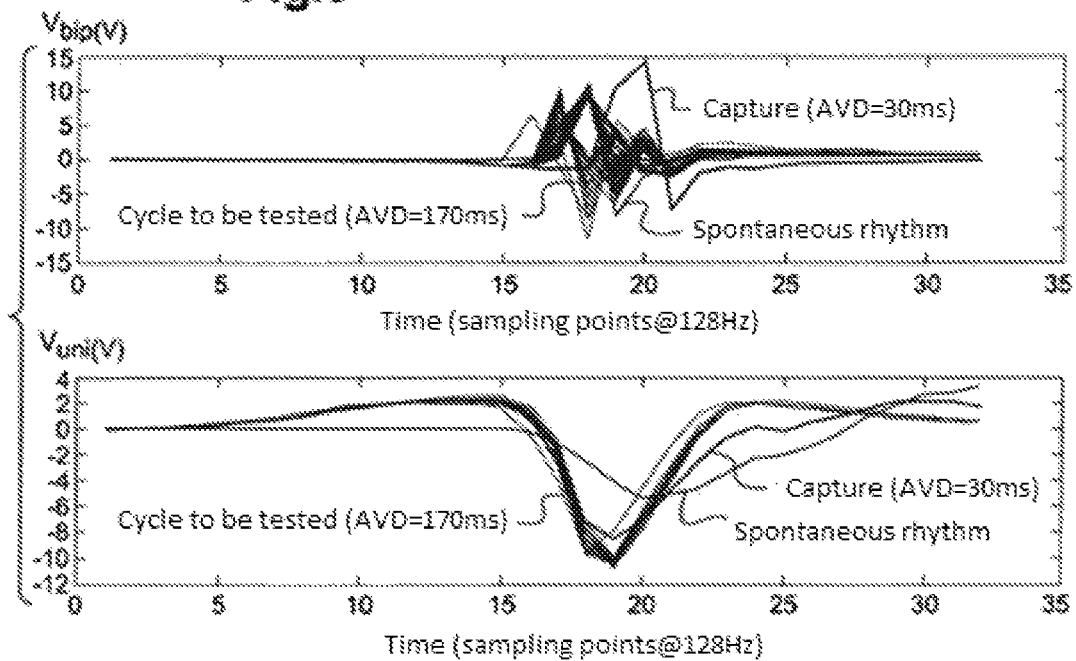

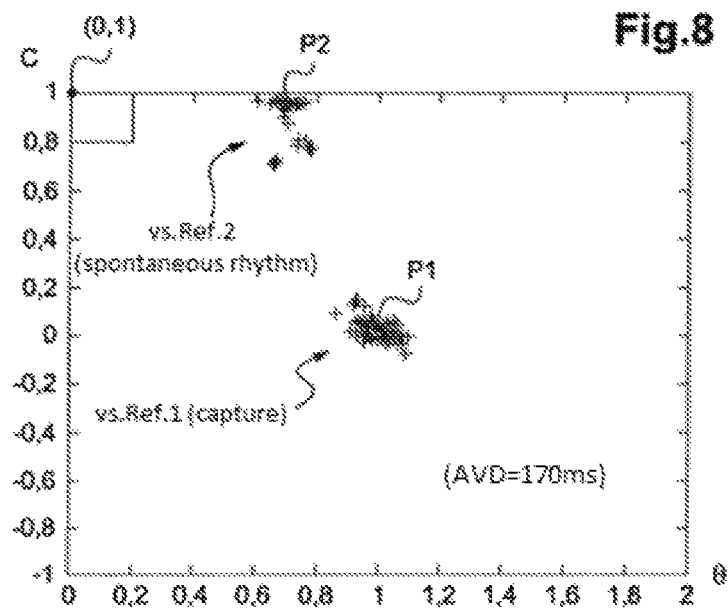
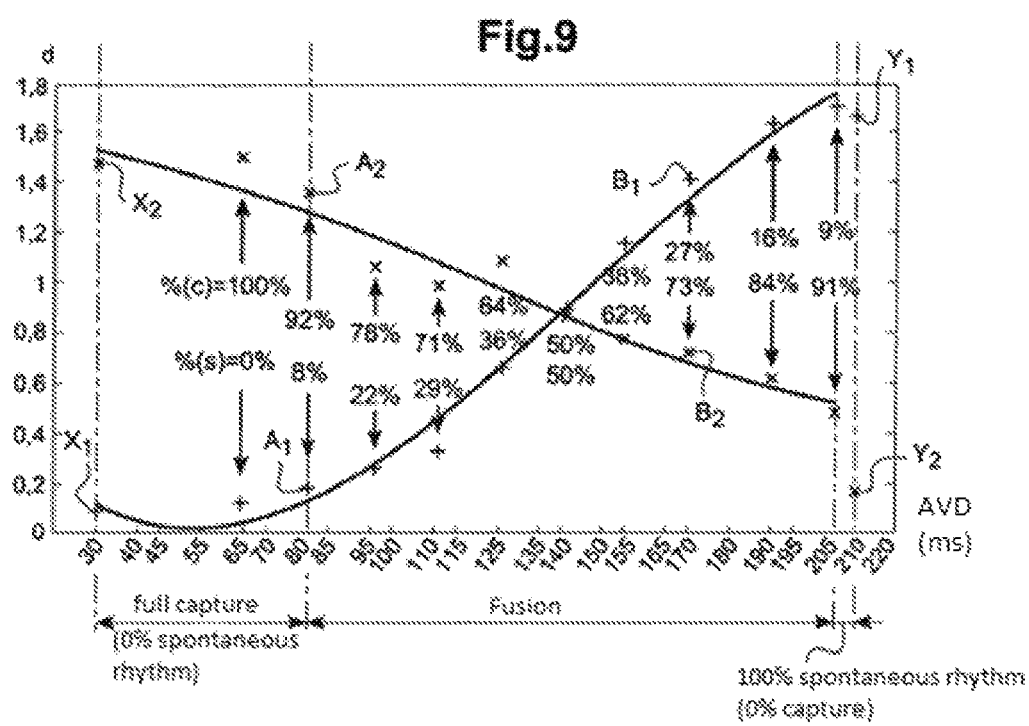

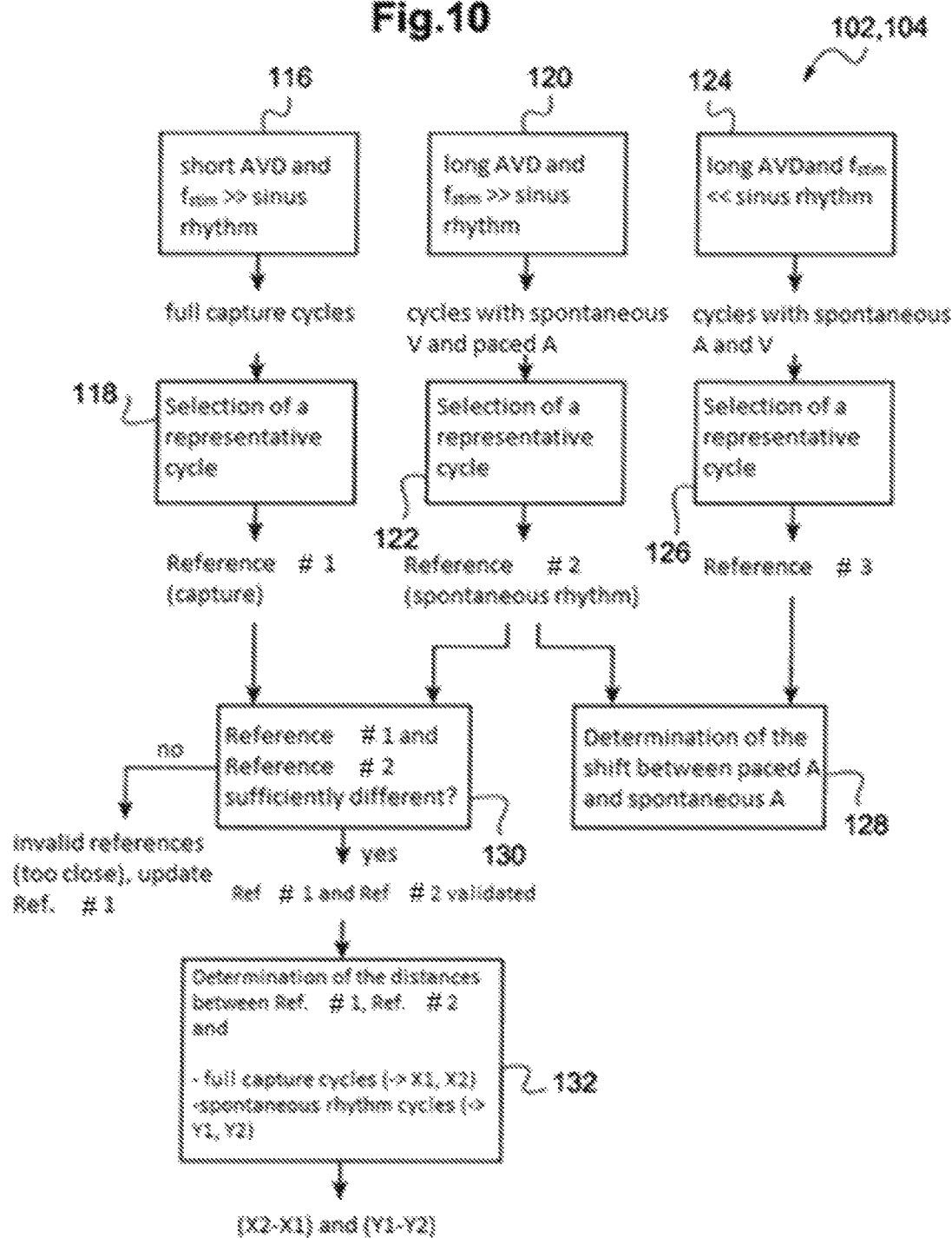

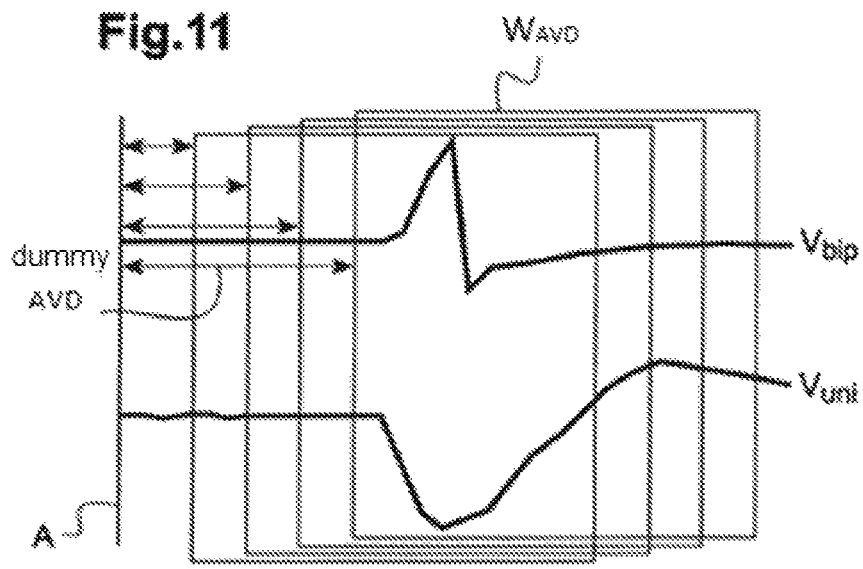
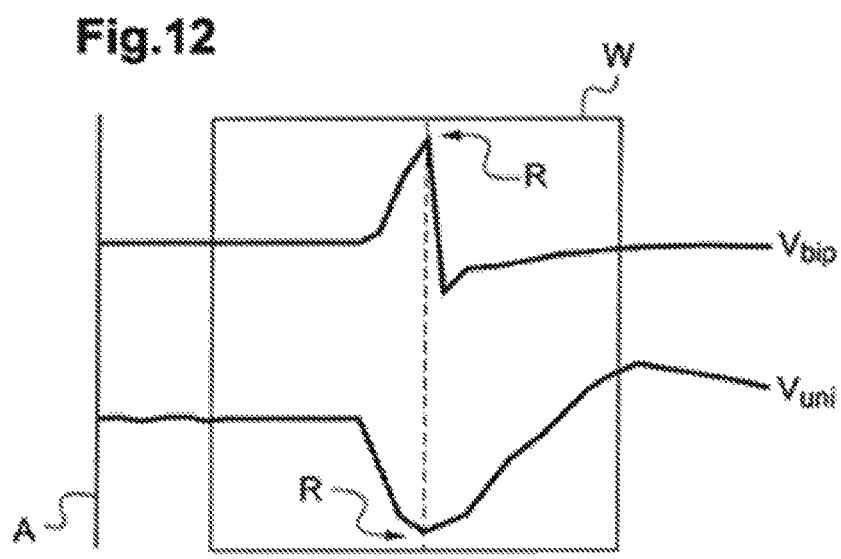

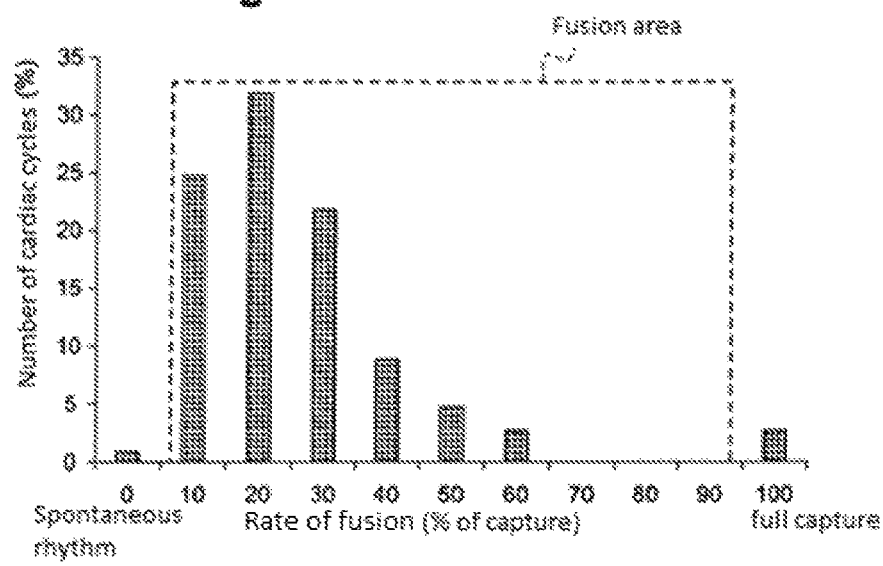
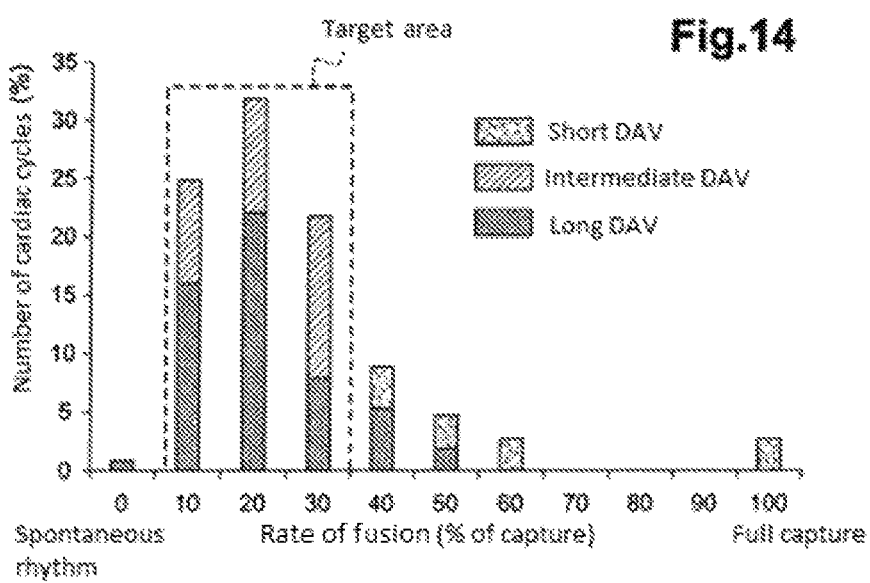

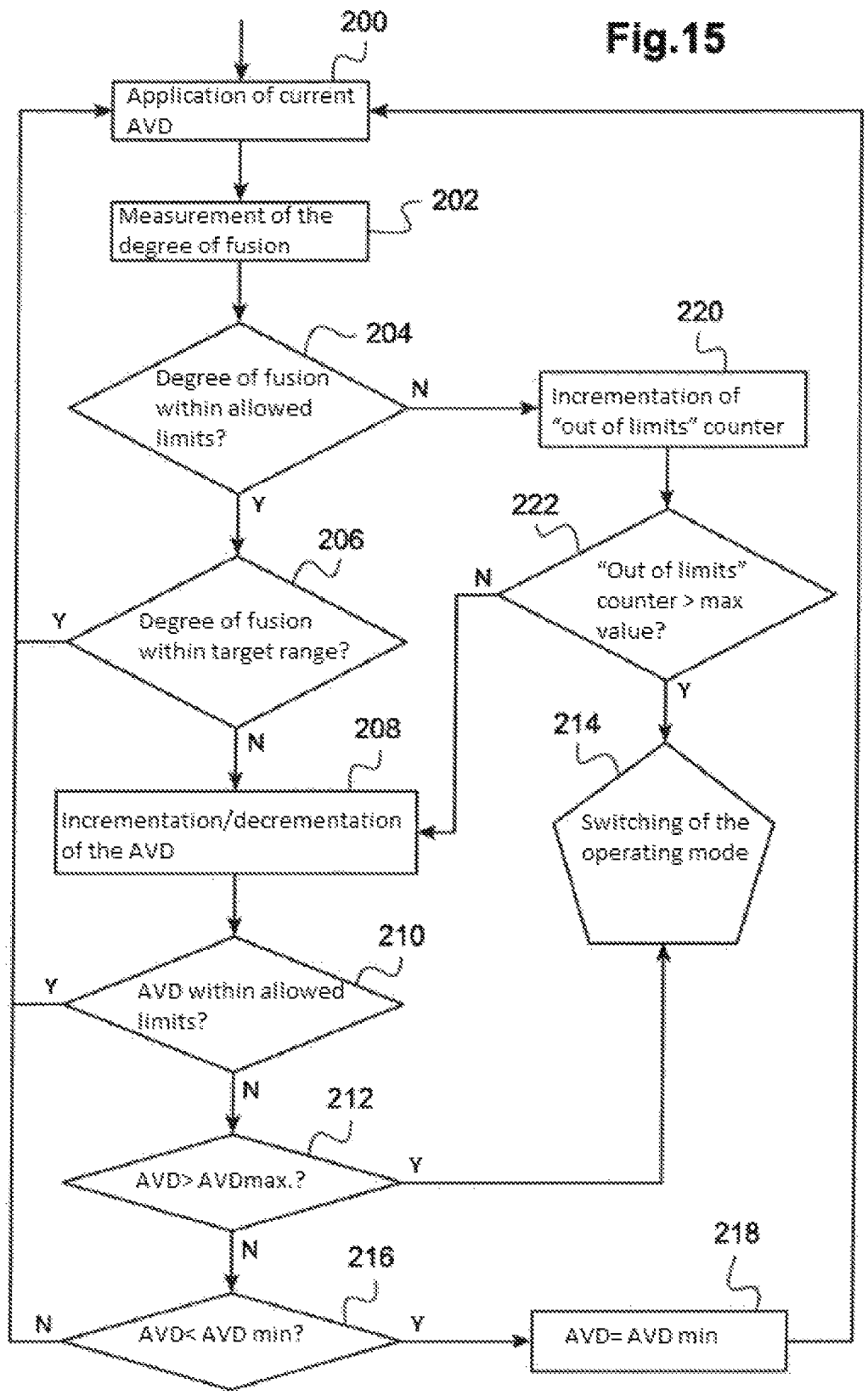

ACTIVE IMPLANTABLE MEDICAL DEVICE SUCH AS A CARDIAC RESYNCHRONISER WITH DYNAMIC ADAPTATION OF AN ATRIOVENTRICULAR DELAY DEPENDING ON A DETECTED AND QUANTIFIED DEGREE OF FUSION

CROSS-REFERENCE TO RELATED PATENT APPLICATIONS

This application is a 371 U.S. National Application of International Application No. PCT/EP2016/080880, filed Dec. 14, 2016, which claims the benefit of and priority to French Patent Application No. 1562739, filed Dec. 18, 2015, which is incorporated herein by reference in its entirety.

BACKGROUND

The invention relates to "active implantable medical devices" as defined by the Council of the European Communities Directive 90/385/EEC of 20 Jun. 1990, more specifically implants designed to continuously monitor the heart rate and to deliver if necessary to the heart pacing electrical pulses in case of disturbance of the heart rate detected by the device.

The invention more particularly relates to resynchronization therapies, known as "CRT" (Cardiac Resynchronization Therapy) or "BVP" (Bi-Ventricular Pacing), consisting in continuously monitoring the heart rate and delivering if necessary to the heart electrical pulses designed to cause a joint contraction of the left and right ventricles (or left and right atria) so as to resynchronize them.

Such a CRT therapy makes it possible to optimize the contraction/relaxation cycle with a direct benefit facilitating the work of the heart, particularly in heart failure pathologies where it is sought to stabilize the cardiac remodeling phenomenon (i.e. all the modifications of the heart generated in response to a pathology, and which is generally associated with a worse prognosis), and even to counter this phenomenon ("inverse remodeling"), with a better prognosis for the patient.

In this context, the invention more precisely relates to the so-called "fusion" situation, that is to say the application in a cavity, more or less concomitantly with a spontaneous depolarization produced naturally by the sinus node (in the case of atrial fusion) and/or by the atrioventricular node (in the case of ventricular fusion), of a pacing intended to induce in the same cavity a depolarization wave called "evoked wave".

In particular, CRT therapy can be implemented with pacing of the left ventricle only when native right atrioventricular conduction is preserved. The right ventricle contracts spontaneously, and the pacing of the left ventricle is controlled so that the latter contracts in synchronism with the right ventricle. This reduces the need for a right pacing, useless or deleterious.

In this case, it is advisable to try to favor the fusion of the pacing of the left ventricle with the spontaneous conduction of the right ventricle.

Note however that this particular case is not limiting the invention, which can also be applied to other pacing situations of a cavity to synchronize with the spontaneous rhythm of the opposite cavity: for example the case of the resynchronization of the two atria between themselves, or that of a pacing of the right ventricle synchronized to the contraction of the left ventricle.

In the presence of a full capture (that is to say when the depolarization of the left ventricle results only from the pacing, the evoked wave preceding any spontaneous depolarization), or if the pacing generates a depolarization too close to the full capture, the atrioventricular delay (AVD) will have to be lengthened to ensure fusion and achieve the desired mechanical effect of resynchronizing both ventricles.

Various fusion situation detection techniques have already been proposed, essentially for conventional "double chamber" pacing devices, i.e. where the device monitors ventricular activity after a spontaneous or stimulated atrial event, and triggers pacing of the right ventricle if no spontaneous ventricular activity has been detected after a certain time. Such detection of a possible fusion is particularly useful in the context of a "capture test" consisting, after having stimulated a cavity, in detecting in this cavity the presence or absence of the evoked wave, in order to determine whether the pacing has been effective or not and to adapt if necessary the efficiency threshold or "pacing threshold", so that the energy delivered be sufficient to induce with certainty an evoked wave, but without being excessive so as not to compromise the lifetime of the device.

EP 2 324 885 A1 (Sorin CRM) describes such a technique, while classifying each cardiac cycle in i) full capture cycle, ii) fusion cycle or iii) cycle with capture loss. This technique has the disadvantage of operating as "all-or-nothing" for fusion: that is to say that everything that does not look like a full capture or a capture loss is considered, failing those, as a fusion situation. In other words, it is a binary classification technique. It is not a quantification technique for fusion which would make it possible to evaluate on a scale the more or less significant time shift between the evoked wave and the wave of the sinus rhythm.

But this document does not plan to apply fusion detection or quantification for controlling a CRT device.

EP 2 756 865 A1 describes another technique which makes it possible not only to determine fusion situations but in addition to quantify a fusion. This technique is based on the analysis of a unipolar EGM with comparison, for each cardiac cycle, of the EGM recorded with two reference signals, to produce two adaptive signed correlation indices (ASCI), between −1 and +1. These indices are then multiplied to reflect the greater or lesser resemblance of the cardiac cycle to the recorded references, an intermediate situation corresponding to a fusion, quantified by the product of the two indices calculated for the cardiac cycle.

However, this technique does not always make it possible to highlight the fusion, as the signal on the unipolar path does not always sufficiently reflect certain characteristic changes in the morphology or temporal synchronism produced by a fusion.

It should hence be noted that in double-chamber pacing fusion is considered as a deleterious phenomenon, and inappropriate in the case of a capture test, a situation which is the exact opposite of that of a CRT device where a fusion between left ventricular pacing and spontaneous contraction of the right ventricle is sought and considered beneficial.

SUMMARY

The aim of the invention is to apply a technique for determining a degree of fusion to control an implanted CRT resynchronization device, in particular a CRT device that can operate in a pacing mode of the left ventricle only, which makes it possible to optimize the operation of this device, notably by dynamically and automatically adjusting the AVD.

More specifically, the invention proposes a device comprising in a manner known per se from the abovementioned EP 2 324 885 A1: ventricular pacing means able to produce pacing pulses intended to be delivered to at least the left ventricle of a patient carrying the device; means for detecting atrial and ventricular events; and means for applying an atrioventricular delay, AVD, between a sensed or stimulated atrial event and the delivery of a ventricular pacing pulse.

According to the invention, this device also comprises: means for quantifying a degree of fusion between the delivery of a pacing pulse to a cavity, left or right, and a spontaneous contraction of another cavity which is opposite, respectively right or left, these means being able to calculate a fusion rate value between two extreme values respectively corresponding to a full capture situation and to a spontaneous depolarization situation of said cavity; and dynamic adaptation means of the AVD able to modify the value of the AVD applied to the delivery of said ventricular pacing pulse, as a function of a comparison made between i) the current value of the fusion rate calculated by the quantifying means, and ii) a target value of the fusion rate.

According to various advantageous subsidiary characteristics:

- the means for quantifying a degree of fusion are means for quantifying a degree of fusion between the delivery of a pacing pulse to the left ventricle and a spontaneous contraction of the right ventricle, these means being able to calculate a fusion rate value comprised between two extreme values respectively corresponding to a full capture situation and a situation of spontaneous depolarization of the left ventricle;
- the means for detecting atrial and ventricular events comprise means able to collect, during the same cardiac cycle, concurrently on different respective paths, at least two different endocardial electrogram signals, EGM, and to derive at least two respective distinct temporal components; and said means for quantifying a degree of fusion comprise means for analyzing the current cardiac cycle, comprising: means able to combine the at least two temporal components in at least one parametric 2D characteristic representative of said cardiac cycle, from the variations of one of the temporal components as a function of the other; and means able to compare the 2D characteristic of the current cycle with at least one reference 2D characteristic obtained previously and stored by the device;
- the means for quantifying a degree of fusion are able to calculate said value of fusion rate over a given number C of cardiac cycles, C≥1, advantageously a variable number, based on a level of activity of the patient;
- the dynamic adaptation means of the AVD comprise means for an incremental modification of the AVD, able to operate: an incrementation of at least one step of the AVD when the current value of the fusion rate has moved with respect to the preceding cycle(s) towards a closer match with said full capture situation, and a decrementation of at least one step of the AVD when the current value of the fusion rate has moved with respect to the preceding cycle(s) towards a closer match with said situation of spontaneous contraction; in this last case, said incrementation/decrementation is an incrementation/decrementation of a variable number of steps, said number of steps being a function of the difference between the current value and the target value of the fusion rate;
- the device further comprises means for comparing the AVD value determined by the dynamic adaptation means of the AVD with an upper limit threshold and means for selectively modifying the operating mode of the device when crossing said upper limit threshold;
- the dynamic adaptation means of the AVD comprise means for limiting said modified AVD value to a minimum floor value;
- the device further comprises: atrial pacing means selectively switchable between a mode with atrial pacing and a mode without atrial pacing; detecting and counting means, in a first counter of the switching operations between modes with and without atrial pacing; detecting and counting means, in a second counter of the occurrences where the variation of the current value of the fusion rate between consecutive cycles exceeds a predetermined threshold; and selective modification means of the operating mode of the device should predetermined respective counting values be exceeded by the first and the second counter;
- the device further comprises: atrial pacing means selectively switchable between a mode with atrial pacing and a mode without atrial pacing; detecting and counting means, in a first counter of the switching operations between modes with and without atrial pacing; detecting and counting means, in a second counter of the occurrences where the variation of the current value of the fusion rate between consecutive cycles exceeds a predetermined threshold; and selective modification means of the operating mode of the device in the event of the first counter exceeding a first predetermined counting value, while the second counter remains below a second predetermined counting value, and vice versa.

BRIEF DESCRIPTION OF THE DRAWINGS

An exemplary embodiment of the invention will now be described with reference to the appended drawings in which the same reference numbers designate identical or functionally similar elements throughout the figures.

FIG. 1 is a general view showing a CRT pacing device with its generator and right and left heart probes implanted in the heart.

FIG. 2 is an example of EGM signals obtained on bipolar and unipolar ventricular pathways, respectively, of one of the probes of FIG. 1.

FIG. 3 illustrates examples of signals collected on a bipolar pathway and a unipolar pathway, for different situations corresponding to a full capture, to a total loss of capture revealing the normal sinus rhythm NSR, and for a number of intermediate cycles to be tested, with possible presence of a more or less marked fusion, for intermediate AVDs between the two situations of capture and loss of capture.

FIG. 8 is a representation, in a two-dimensional space, of scatter plots corresponding to various recorded values of pairs of descriptors, over a number of current cycles, when compared with the two references corresponding respectively to a capture and a sinus rhythm.

FIG. 9 is a representation showing the variations of the distance between the points in the space of FIG. 8 and the origin of this same space, for increasing values of the AVD.

FIG. 10 is a flowchart showing the sequence of steps performed during the prior computation of the two references subsequently used for determining the degree of fusion of a current cycle.

FIGS. 11 and 12 illustrate two different windowing techniques for comparing the cycle to be tested with the sinus rhythm reference.

FIG. 13 is a histogram showing the distribution of the measured fusion rates at each cardiac cycle, evaluated statistically over a period of several weeks.

FIG. 14 shows a series of superimposed histograms of the same type as that of FIG. 13, recorded for different durations of atrioventricular delay.

FIG. 15 is a flowchart giving an example of a sequence of steps of the dynamic adjustment method of the AVD according to the invention.

DETAILED DESCRIPTION

Figure 4:
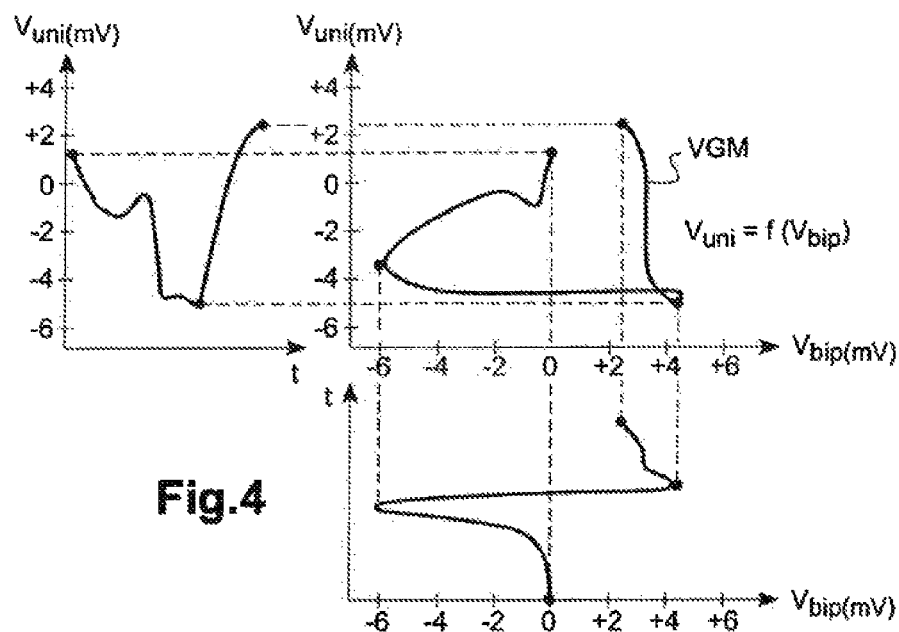
FIG. 4 illustrates how to combine together the bipolar and unipolar signals collected in the same ventricular cavity to construct a two-dimensional vectogram type characteristic.

An exemplary embodiment of the technique of the invention will now be described.

With regard to its software aspects, the invention can be implemented by appropriate programming of the control software of a known stimulator, for example of the pacemaker, resynchronizer and/or defibrillator type, comprising means of acquisition of a signal supplied by endocavitary probes and/or one or more implanted sensors.

The invention can notably be applied to implantable devices such as those of the Reply CRT-P, Paradym CRT-D, Intensia CRT-D and Platinum CRT-D classes, produced and marketed by Sorin CRM, Clamart, France.

These are programmable microprocessor devices having circuits for receiving, shaping and processing electrical signals collected by implanted electrodes, and delivering pacing pulses to these electrodes. It is possible to transmit by telemetry to such devices software that will be stored in memory and executed to implement the functions of the invention which will be described below. The adaptation of these devices to the implementation of the functions of the invention is within the abilities of those skilled in the art and will not be described in detail.

The method of the invention is implemented mainly by software means, using appropriate algorithms executed by a microcontroller or a digital signal processor. For the sake of clarity, the various processing steps applied will be broken down into and schematized by a certain number of distinct functional blocks presented in the form of interconnected circuits, but this representation is however only illustrative, since these circuits comprise common elements and correspond in practice to a plurality of functions generally executed by the same software.

FIG. 1 illustrates the pacing configuration to which the invention is applied, namely biventricular pacing, especially in order to restore synchronization between the two ventricles.

A pulse generator 10 is associated with a first probe 12 implanted in the right ventricle 14. The head of this probe comprises two electrodes, namely a distal electrode (tip) 16 and a proximal electrode (ring) 18. A second probe 20 is provided with distal 22 and proximal 24 atrial detection electrodes located at the right atrium 26 for the detection of signals in this cavity and the possible application of atrial pacing (alternatively, these atrial electrodes 22, 24 may be floating electrodes placed on the probe 12 at the atrium). In some configurations, the right ventricular probe 12 can also feature a ventricular coil 28 forming a defibrillation electrode while also making it possible to collect an endocavitary signal (this coil may then be used in place of the proximal electrode (ring) 18).

For left ventricle pacing, the pulse generator 10 features a third probe 30, for example a probe placed in the coronary network, having one or more electrodes 32, 34 positioned in the vicinity of the left ventricle 36 (in the case of a "multi-electrode" left probe, the left probe may also include one or more intermediate electrodes located in a median position between the electrodes 32 and 34). It is thus possible to ensure the pacing concurrently, or with a slight controlled temporal shift (interventricular delay DVV), of the two right and left ventricles, so as to restore the synchronization between these two cavities and improve the general hemodynamics of the patient. In the case of a left multi-electrode probe, one can also apply a multisite pacing on the left to treat an intraventricular synchronism disorder.

It is also possible—and this is the case that is specifically considered by this invention—to stimulate the left ventricle alone when native right atrioventricular conduction is preserved. In this case the right ventricle contracts spontaneously, and the pacing of the left ventricle is controlled in such a way that the latter contracts synchronously with the right ventricle. This reduces the need for a right, useless or deleterious, pacing.

With regard specifically to left ventricle pacing, it is possible to use a bipolar (between the two electrodes 32 and 34 of the probe 30) or unipolar (between one of the electrodes 32 or 34 and the housing can) configuration of the generator 10, or else between one of the electrodes 32 or 34 and an electrode of the probe 12. A quadrupolar probe can also be used for these same purposes. Corresponding "pacing vectors" are referenced as numerals 38 and 40 in FIG. 1. These same vectors can also be used for collecting a left ventricular depolarization signal. Note that in the case of a multipolar probe there exist a large number of possible bipolar and unipolar vectors, defined from each of the electrodes (one can also simultaneously use several left vectors, in the aforementioned hypothesis of multisite pacing on the left).

As will be described in detail below, the technique of the invention implements a combination of two different endocavitary electrogram signals collected simultaneously, in particular signals from the same ventricular cavity, for example the right ventricle.

FIG. 2 illustrates an example of EGM plots, Vbip and Vuni, observed respectively on the ventricular bipolar pathway and the unipolar ventricular pathway according to the configuration shown in FIG. 1.

EGMs collected for this purpose in the right ventricle may include, for example:
- a right ventricular component Vbip, derived from a bipolar near-field EGM signal collected between the distal electrode 16 and the proximal electrode 18 of the right ventricular probe 12, and
- another right ventricular component Vuni, derived from a bipolar far-field Vuni EGM signal collected between the defribrilation coil 36 of the right ventricular probe 12 and the metal housing of the generator 10.

Other configurations may be used, from signals of the far-field type (for example between one of the electrodes 16 or 18 and the housing 10, or between the electrodes 18 and 32) and of the near-field type (for example between two electrodes 32 and 34 of the same ventricular probe).

The FIG. 3 illustrates examples of signals collected on a bipolar pathway (Vbip) and on a unipolar pathway (Vuni), in different situations corresponding to a full capture, to a total loss of capture revealing the spontaneous ventricular rhythm, and for a certain number of intermediate cycles to be tested, with the presence of a possible more or less marked fusion, for intermediate AVDs between the two situations of capture and loss of capture.

It can be seen in particular in this figure that the information is not the same on the bipolar and unipolar pathways and that, for example, the fusion cycles (in this example, with an AVD at 170 ms) are much closer morphologically to the spontaneous rhythm than to the capture on the bipolar EGM, and much closer to the capture on the unipolar EGM.

Considering only the unipolar EGM—as in the technique described in the aforementioned EP 2 756 865 A1—the difference is far less marked between fusion cycles and reference cycles with full capture, which would lead, if we were to quantify the fusion, to a percentage of fusion (expressed as a capture percentage) much larger than in actual fact.

For these reasons in particular, it is advantageously provided in this invention to use a 2D representation of the two EGMs.

The combination of the two bipolar and unipolar components into a single characteristic makes it possible to have a reference containing in a more general way all the information available from the EGM, which makes it possible to quantify in a precise and robust way a possible fusion present with the current cardiac cycle.

More precisely, the two bipolar and unipolar signals are combined into a single characteristic of the "cardiac loop" or "vectogram" (VGM) type, which is the representation in a two-dimensional space of one of the two EGM signals (on the y-axis—ordinate) as compared to the other (on the x-axis—abscissa). Each cardiac cycle is then represented by a vectogram in the thus defined plane {Vbip, Vuni}, a vectogram whose geometry (curve shape) thus leaves aside the temporal dimension—which comes into play only as a parameter describing the way in which the curve is travelled.

It should be emphasized that this "vectogram" (VGM), which is obtained based on electrogram signals (EGM) from intracardiac probes, should not be confused with the "vectocardiogram" (VCG), which is obtained based on electrocardiogram (ECG) signals from external electrodes placed on the patient's thorax.

The construction of a VGM and its analysis to quantify cardiac data are described for example in Milpied et al., "Arrhythmia Discrimination in Implantable Cardioverter Defibrillators Using Support Vector Machines Applied to a New Representation of Electrograms," *IEEE Transactions on Biomedical Engineering*, June 2011, 58 (6): 1797-1803.

In addition, the analysis of a VGM has already been proposed, as explained in the introduction, by EP 2 324 885 A1 (Sorin CRM) for deciding on a fusion suspicion in order to invalidate a capture test.

Note also that the "bidimensional" or "two-dimensional" analysis (2D) mentioned here should not be understood in a way that is in itself limitative. The technique described can indeed just as well be applied to an analysis in a multidimensional higher order space (3D or more), by extrapolating the teachings of the present description to a situation where EGM signals from one and the same cavity are collected simultaneously on three or more channels.

As shown in FIG. 4, EGM signals Vuni(t) and Vbip(t) are collected and sampled, and the successive samples of the two components are stored and then combined together to produce a parametric curve (the VGM characteristic) of the VGM type=(Vbip(t), Vuni(t)) or {x=Vbip(t), y=Vuni(t)}.

This curve is a curve parameterized by time, drawn from the variations of one of the temporal components (Vuni) as a function of the other (Vbip). It constitutes a representative vectogram (VGM) of the cardiac cycle to be analyzed and will also be designated as a "parametric 2D characteristic". It graphically presents the shape of a loop, the time appearing only in the way in which the loop is travelled over the duration of the cycle.

Figure 5:
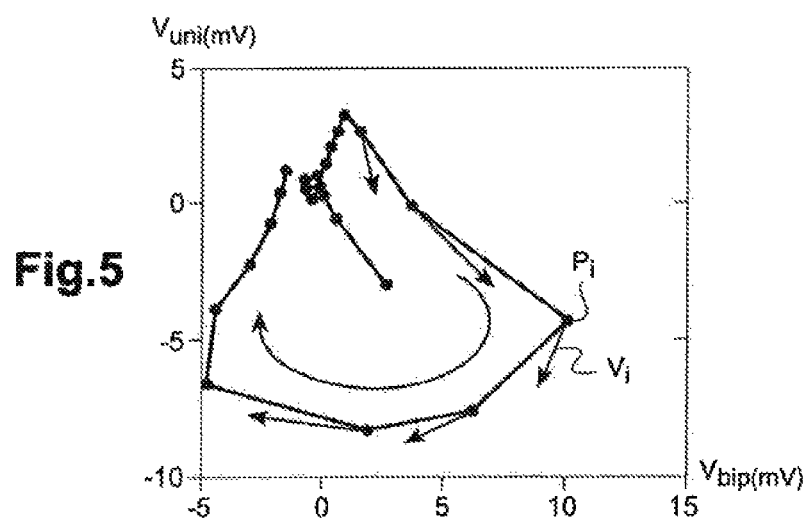
FIG. 5 is an example of a sampled vectogram obtained for a cardiac cycle sampled at 128 Hz, representing velocity vectors at various successive points.

In practice, as shown in FIG. 5, the sampling produces a VGM with an open polygon shape where each vertex corresponds to a sampling point of the signal measurement, Vuni and Vbip, of the EGM. In the example of FIG. 5, the sampling is done at a frequency of 128 z, which gives about 22 measurement points for a time interval of 164 ms, which are all values that can be stored in memory to be analyzed (concretely, it is possible to keep in memory a greater number of points, for example 60 points, the comparison between two vectograms being however operated on a more limited number of points, typically 11 or 21 points).

The FIG. 5 also shows the appearance of the velocity vector $V_i$ at various successive points Pi of the VGM for a sampling frequency of 128 Hz. At a given point, the velocity is a vector datum (velocity being defined by its direction and its norm), and the velocity vector can be calculated at each point of the VGM from a discrete filter which approximates the first derivatives Vbip(t)/dt and Vuni(t)/dt which, for a sampled characteristic, can be calculated from the previous point and the next point on the curve.

The collected VGM characteristic is stored as a series of descriptor parameters based on the velocity vectors at each point of the curve and including the speed vector norm and the direction of this velocity vector, i.e. angle that it forms with respect to the VGM abscissa axis.

In order to quantify the fusion, a morphological comparison is advantageously made between, on the one hand, the current VGM (stored as the values of the norms and the angles of the velocity vectors at the different sampling points) and, on the other hand, two reference VGMs (stored in the form of homologous descriptors), one obtained in a situation of full capture of the ventricle and the other obtained in a situation of exclusively spontaneous rhythm in the ventricle, that is to say with a 0% fusion rate in terms of capture percentage.

The comparison between the VGM of the current cycle and these two reference VGMs makes it possible, if a fusion (that is to say a situation which is neither that of a full capture nor that of a spontaneous ventricular rhythm) is detected, to evaluate a fusion rate, thus making it possible to quantify by a metric the more or less important temporal shift between the evoked depolarization wave following the pacing, and the spontaneous depolarization wave related to the natural rhythm.

The comparison between the VGM of the current cycle and one or other of the reference VGMs will consist of quantifying their similarities from:
- the correlation coefficient C between the norms of the respective velocity vectors of the current VGM and the reference VGM, and
- the average value θ of the angle between the respective velocity vectors of the current VGM and the reference VGM.

It can be considered that the curves look alike if C (which reflects the correlation between the norms of velocity vectors) is sufficiently large, that is to say close to the unit, and θ (which reflects the angular differences in directions) is sufficiently small, that is close to zero. The further the value of C departs from 1 and the value of θ from 0, the more the two VGMs will be dissimilar.

It will be noted that the use of the parameters C and θ to make the comparison between two VGMs is not limiting, and that other parameters can be used. Likewise, the combined use of C and θ is particularly advantageous, but it would also be possible to evaluate the likeness of VGMs from only one of the two parameters C or θ, or from a larger number of parameters, three parameters and more. However, descriptors C and θ are preferred because of their low sensitivity to artefacts and the relative ease of calculating them.

Figure 6:
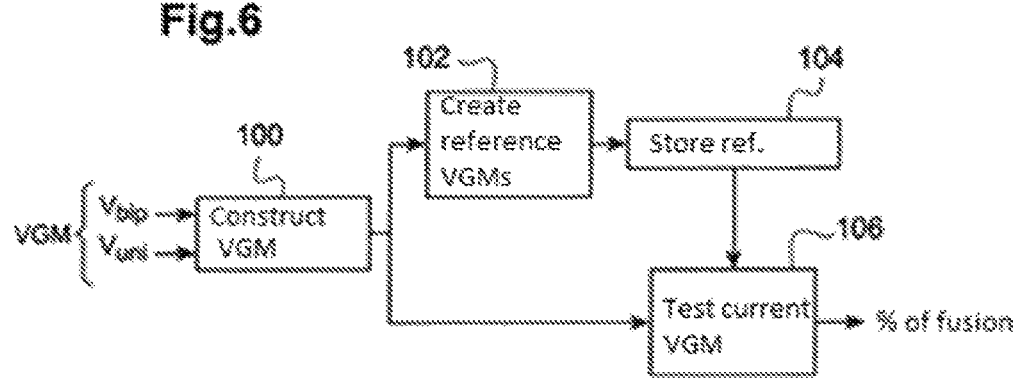
FIG. 6 is a block diagram illustrating the implementation of a preferred technique for quantifying the degree of fusion.

FIG. 6 illustrates in a very general way how this preferred quantization technique is implemented.

From the bipolar and unipolar EGMs collected, a VGM is constructed (block 100). Beforehand, two reference VGMs are constituted under stable conditions (slow sinus rhythm, preferably at night) (block 102, detailed in FIG. 10) and stored in memory (block 104). The current VGMs will subsequently be compared (block 106) to the two stored reference VGMs, to output a metric quantifying a fusion rate between 0 and 100%.

The "rate of fusion" can be expressed simply in terms of the rate of spontaneous rhythm—that is to say that a 0% fusion rate will correspond to a full capture and a 100% fusion rate will correspond to a situation of exclusively spontaneous rhythm. This fusion rate can also be expressed with respect to a capture situation, the fusion rate then varying from 100% to 0% in the opposite direction.

Figure 7:
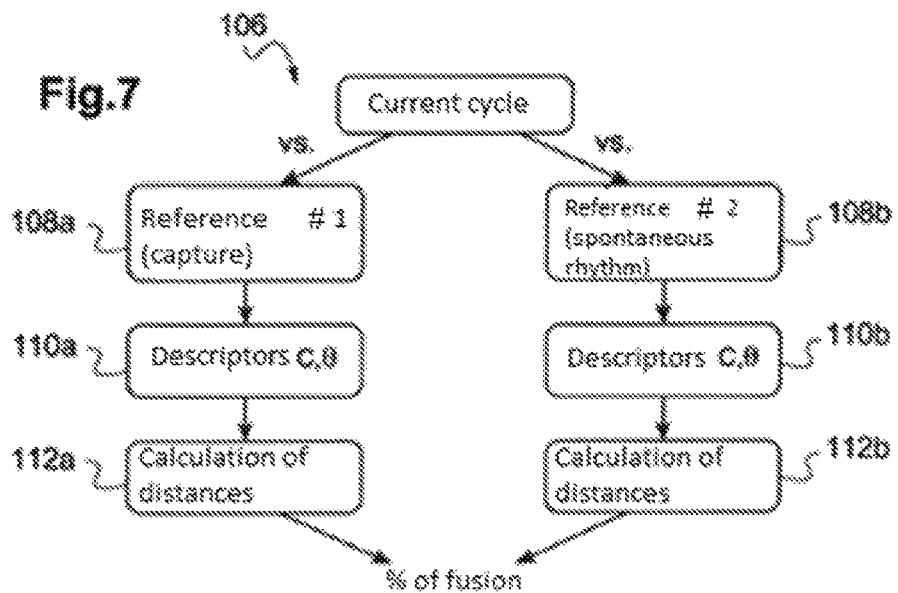
FIG. 7 is a simplified flowchart showing the sequence of steps performed for the analysis of a current cycle.

FIG. 7 illustrates the test of the block 106, in the form of a simplified flow chart showing the sequence of steps performed for the analysis of a current cycle.

The VGM of the current cycle is compared to both the reference VGM corresponding to a complete capture situation, hereinafter "Reference #1" (block 108a), and to the VGM corresponding to a situation of spontaneous ventricular rhythm, hereinafter "Reference #2" (block 108b).

These two comparisons produce two respective pairs of descriptors C and θ (blocks 110a and 110b), which can be represented in a two-dimensional space shown in FIG. 8. The next step (blocks 112a and 112b) consists in calculating the distances of the various points [C, θ] of the two-dimensional space corresponding to the descriptors obtained with respect to the point of origin [0, 1] of this same space, in order to determine, from these distances and as will be described below, a metric quantifying a fusion rate of the current cycle.

FIG. 8 illustrates in the two-dimensional space whose two dimensions correspond to the two descriptors C and θ, an example of distribution of the points obtained for a few tens of current cycles with the same AVD, adjusted in this case to 170 ms. This example shows two scatter plots, one obtained by comparing the current cycles with Reference #1 (full capture), the other by comparing them with Reference #2 (spontaneous ventricular rhythm). The points P1 and P2 indicate the respective barycentres of these two scatter plots.

The point [0, 1] corresponds to an ideal theoretical situation where the current cycle would be identical to one or the other of the reference cycles, with a correlation coefficient C equal to the unit and an average angle θ equal to zero between the respective velocity vectors of the two VGMs.

For comparing the VGMs of the current cycles with each of the References 1 and 2 the evaluation is carried out as follows:
- either by comparison with predetermined thresholds on C and/or θ: for example, the curves are considered to look alike if C>Threshold 1 and θ<Threshold 2;
- or based on a relation between C and θ: one considers for example that the curves look alike if C>θ;
- or advantageously by using the distance calculated in the plane [C, θ] of the descriptors between the current point and the point [0, 1]: the smaller this distance, the more the VGMs look alike.

Thus, in the illustrated example, when considering the distance between each of the points P1 and P2 and the point of origin [0, 1], we see that the results of the two respective comparisons show that the scatter plot of the comparison with Reference #2 (spontaneous rhythm) is closer to this origin than the scatter plot of the comparison with Reference #1 (full capture), which means that the current cycles are, in fusion, closer to a spontaneous ventricular rhythm than a full capture—so with a fusion rate, expressed as a percentage of capture, smaller than 50%—but however not sufficiently close to the point [0, 1] to infer that it is a purely spontaneous rate.

FIG. 9 is a representation in which the AVD has been varied between all possible adjustment values, from a minimum value of the AVD=30 ms producing in all circumstances a full capture of the ventricle, up to a maximum value of the AVD sufficiently long for the spontaneous rhythm to express itself. On the y-axis (ordinate) is plotted the distance d between the origin [0, 1] of the two-dimensional space of FIG. 8 and the point [C, θ] resulting from the comparison with Reference #1 (points represented by "+" signs) or with Reference #2 (points represented by "x" signs).

For a minimum AVD, AVD=30 ms in full ventricular capture, we obtain respectively the X1 and X2 marks, and for a maximum AVD (here 210 ms) we obtain the respective marks Y1 and Y2.

The figures also show the percentages of fusion, expressed in terms of percentages of capture ("% (C)") and in terms of percentages of spontaneous rhythm ("% (S)").

If the current fusion cycle is closer to a capture than to a spontaneous rhythm (left side of FIG. 9, case of marks A1 and A2), then the percentage of capture is greater than 50% and the percentage of spontaneous rhythm is smaller than 50%. Conversely, if the current fusion cycle is closer to a spontaneous rhythm than a capture (right side of FIG. 10, case of marks B1 and B2 corresponding to points P1 and P2 of FIG. 9), then the percentage of capture is smaller than 50% and the percentage of spontaneous rhythm is greater than 50%.

To quantify the degree of fusion, we will consider the difference between the X1 and X2 marks obtained in full capture, which difference in this example is of the order of X2−X1=1, 4. In the same way, the difference between the marks Y1 and Y2 in full spontaneous rhythm is of the order of Y1−Y2=1, 6. In the case of a current fusion cycle closer to capture than to spontaneous rhythm (marks A1 and A2, where A2>A1), we should always have A2−A1<1, 4, thus moving away from the capture (A1>X1) and getting closer to the spontaneous rhythm (A2<X2).

If A2>A1 and A2−A1<X2−X1 and if A1>X1 and A2<X2 (with a tolerance, for example a tolerance of 0, 1), then the capture percentage will be:

$$50+[50*(A2-A1)/(X2-X1)]$$

In the opposite case, no degree of fusion will be calculated for the cycle considered, which may correspond to an extrasystole and not follow the expected progression. A counter can be incremented, because if this case is too frequent, it can mean that references and reference distances X2 and X1 have to be updated.

It can be considered that a capture percentage greater than a given threshold, for example greater than 90%, corresponds to a full capture situation, and not to a fusion.

The percentage of spontaneous rhythm can then be calculated as:

$$100-\text{the percentage of capture.}$$

If the current fusion cycle is closer to the spontaneous rhythm than to the capture (marks B1 and B2, where B1>B2), then in order to calculate the percentage of spontaneous rhythm one can base oneself on the distance between the marks in spontaneous rhythm Y1 and Y2.

For a current fusion cycle, a value of B1−B2<1, 6 should always be obtained and one should get closer to the capture (B1<Y1) and move away from the spontaneous rhythm (B2>Y2).

If B1>B2 and B1−B2<Y1−Y2 and if B1<Y1 and B2>Y2 (with a tolerance, for example a tolerance of 0, 1), then the percentage of spontaneous rhythm will be:

$$50+[50*(B1-B2)/(Y1-Y2)].$$

Otherwise, no degree of fusion will be calculated for the cycle considered. A counter can be incremented, because if this case is too frequent, it can mean that references and reference distances Y2 and Y1 have to be updated.

It can be considered that a percentage of spontaneous rhythm greater than a given threshold, for example greater than 95%, corresponds to a situation of spontaneous rhythm and not of fusion.

The capture percentage can then be calculated as:

$$100-\text{the percentage of spontaneous rhythm.}$$

The final fusion rate can be expressed either in terms of capture rate, or in terms of spontaneous rhythm rate, or by a combination of these two rates.

With reference to FIGS. 10 to 12, the manner in which the two references used for the determination of the fusion rate can be obtained will now be described.

These references are created and updated periodically and in stable conditions (especially at night), for example once a day or once a week.

To establish the full capture reference (Reference #1), the AVD is programmed to the shortest possible value, for example AVD=30 ms, preferably with pacing of the atrium at a pacing frequency significantly greater than the sinus rhythm (block 116) so as to move away as far as possible from the conditions of occurrence of a possible fusion.

Under these conditions, a plurality of full capture cycles are recorded, which are then compared to establish or select a single representative cycle (block 118). A first method consists in recording several VGMs and comparing them in pairs, then checking that a minimum number of VGMs, for example two VGMs look alike. Another method is to look for, while recording the cycles, two VGMs that look alike, with a maximum number of VGMs to be tested, for example five VGMs; If there is a sufficient resemblance between the cycles, then Reference #1 is created and stored, either by selecting one of the cycles, or by averaging the cycles that look alike.

For the spontaneous rhythm reference (Reference #2), a very long AVD is programmed, for example AVD=300 ms, so as to let the spontaneous rhythm come to expression before any pacing (block 120). A plurality of cycles are thus produced in the same way as for full capture cycles, and Reference #2 is similarly created by determining a single representative cycle (block 122) after comparing the different cycles produced.

However, to establish this Reference #2, a larger measurement window is required because the portion of the EGM used for subsequent comparison of the cycles to be tested will depend on the AVD of said cycles to be tested. Moreover, the moment in which the depolarization takes place is not the same in the case of a stimulated atrial event (event A) as in that of a spontaneous depolarization of the atrium (event P).

A first possibility is to establish two distinct references for spontaneous ventricular rhythm, one with pacing of the atrium and the other with spontaneous depolarization of the atrium (sinus rhythm).

Another preferred solution is to establish a single reference, for example with stimulated depolarization of the atrium, and to allow for a time compensation value or offset, determined as being the difference in conduction times in the ventricle observed for a spontaneous depolarization of the atrium (P) and for a stimulated depolarization of the atrium (A): offset=AR−PR.

This shift is established by temporarily programming a long AVD with a pacing frequency much lower than the sinus rhythm (block 124), then selecting, as previously, a representative cycle (block 126) to obtain a provisional reference (Reference #3) for determining the said shift (block 128).

In a simplified variant, this shift can be established during the calculation of Reference #2 by measuring intervals AR, as well as intervals PR, without Reference #3, but only under conditions of long AVD and low frequency pacing (block 124), applied over a few cycles (8 cycles for example), and by considering the difference between the average value of the AR intervals and the average value of the PR intervals. Once the two references, Reference θ and Reference #2, have been established, one last step consists in comparing these two references by applying a dummy AVD of 30 ms and an offset if necessary (so that the condition of the atrium and the AVD be the same). The two references are then compared (block 130):

if Reference #1 is in full capture, then the depolarization of Reference #2 must take place later than that of Reference #1 (no overlap in time), as the comparison of the curves must result in a significant difference between the references. The references are then validated and analyzed (block 132) so as to determine the references X1, X2 and Y1, Y2 and the deviations X2−X1 and Y1−Y2 (block 132);

if, on the other hand, the distance in the two-dimensional space of the descriptors C and θ between the current point and the point [0, 1] is less than a given threshold, for example smaller than the unit, then it is considered that the references are too close, Reference #1 being probably already in fusion and not in full capture. It will therefore not be possible to determine a correct degree of fusion and Reference #1 is then invalidated as a full capture reference.

In the latter case, it is possible to repeat the calculation of Reference #1 by producing a plurality of additional cycles in VVI mode at a frequency higher than the patient's base frequency, for example at a frequency of 100 bpm allowing a reference in full capture to be recovered. It will then suffice to compare all the cycles thus obtained with Reference #2 and to take the one which differs from it the most while being very close to the response evoked with an AVD=30 ms, this selection being made as previously by applying thresholds to the values of C and θ. Another possibility is to use an older Reference #1 (if it exists) and revalidate it with the new Reference #2. FIGS. 11 and 12 illustrate two different windowing techniques for comparing the cycle to be tested with the reference in spontaneous rhythm.

Indeed, when it comes to comparing a stimulated current cycle with the reference in spontaneous rhythm, an AVD is applied to the current cycle whereas the cycles of the reference were obtained without an AVD.

As illustrated in FIG. 11, to compare cycles to be tested stimulated with variable AVDs to the Reference #2 in spontaneous rhythm, the device applies a "dummy AVD" (dummy, since spontaneous rhythm is applicable here) that is added to the offset in case of non-pacing of the atrium, thus producing a shift in the window $W_{AVD}$ of bipolar and unipolar EGMs analysis, thus providing a unique Reference #2 regardless of the value of the programmable AVD (typically, from 30 to 250 ms). For example, to conduct a test of a cycle with pacing of the atrium and an AVD of 12 ms, Reference #2 will be used with a dummy AVD of 125 ms. Indeed, the sequencing of the EGMs with respect to the atrial marker A is as important as the morphology of the signals when comparing two VGMs obtained from respective bipolar and unipolar EGM signals.

The FIG. 12 illustrates an alternative consisting in using, instead of the moving window of FIG. 11, a single window W centered on the characteristic peak (extremum R) of the EGM signal Vbip or Vuni, independently of the type of spontaneous or stimulated atrial depolarization. However, this solution is not optimal insofar as it does not take into account the conduction delay.

Application of the Measurement of the Fusion Rate to the Control of the AVD in a CRT Stimulator with Pacing of the Left Ventricle A specific example of exploiting the fusion rate data obtained dynamically at each cardiac cycle will now be described as specified above.

The application depicted here is, however, not limited to this particular fusion rate determination technique, and may be implemented on the basis of fusion rate measurements obtained in another manner.

More specifically, the application that is the subject of the invention is in the context of a CRT therapy with pacing of a cavity to synchronize with the spontaneous rhythm of the opposite cavity.

In the following example, a pacing of the sole left ventricle synchronized to the spontaneous depolarization of the right ventricle will be considered, but this case is non-limiting, the invention being also applicable, as indicated in the introduction, for example in the case of the resynchronization of the two atria between themselves, or that of a pacing of the right ventricle synchronized to the spontaneous depolarization of the left ventricle.

This therapy can be implemented when the native right atrioventricular conduction is preserved: the right ventricle then contracts spontaneously, and the pacing of the left ventricle is triggered and controlled in such a way that the latter contracts in synchronism with the right ventricle.

It should be noted that this technique can be implemented both from a spontaneous contraction of the atrium, the rhythm then being the natural spontaneous sinus rhythm, and from a contraction of the atrium triggered by a pacing pulse generated by the implanted device.

In any case, as it is assumed that the right atrioventricular conduction is preserved, since a contraction of the atrium, either stimulated (event A) or spontaneous (event P) has been obtained, the right ventricle will contract spontaneously (event R) after a PR or AR interval following the contraction of the right atrium.

In such a situation, it is advisable to try and promote the fusion of left ventricle pacing with the spontaneous conduction of the right ventricle.

The atrioventricular delay AVD, which controls the pacing moment for the left ventricle, must therefore be adapted to guarantee the fusion and obtain the desired mechanical effect of resynchronization of the two ventricles.

However, in practice, the degree of fusion can vary from one cardiac cycle to another depending on the programmed mode of operation of the device, the patient's activity, etc.

The FIG. 13 is a typical histogram of fusion rate values (expressed as a capture percentage) recorded over a long period, in the order of three months. The "fusion area" corresponds to the area in which one considers that there is a more or less significant fusion, the extreme classes 0 and 100 corresponding respectively to a pure spontaneous rhythm and to a complete capture, being considered as an absence of fusion.

In the case of CRT pacing of the left ventricle, it will be sought to restrict this fusion area to a "target area" corresponding to a reduced number of classes of the histogram, for example a degree of fusion between 10% and 30% (expressed as a capture percentage). This target area, corresponding to an optimal degree of fusion sought, will vary according to the application, and will be determined a priori from hemodynamic measurements (echography, measurement of dP/dtmax, etc.), electrical measurements (electrocardiogram, measurement of the PR intervals, of the conduction time LVp-RVs) or measurements delivered by other sensors, or from values set manually by the physician. The target value, corresponding to the optimal degree of fusion, may be given a certain tolerance to take account of measurement and cycle-to-cycle accuracy variations: for example, for a 20% fusion rate target (as a capture percentage), a tolerance of 20±10% can be provided, i.e. a target area between 10 and 30% of the fusion rate (as a capture percentage).

The FIG. 14 illustrates a histogram of the same type as that of FIG. 13, where a target area corresponding to this example has been delimited, namely a 10 to 30% fusion rate (as a capture percentage).

In practice, if the AVD is changed, this histogram also changes:
for a short AVD, a significant number of cardiac cycles are outside the target area;
For an AVD of intermediate value, almost all cardiac cycles are within the target area;

For a long AVD, just as in the case of the short AVD, there is a non-negligible number of cycles outside the target area.

The purpose of the technique depicted here, based on a dynamic measurement of the fusion rate, performed cycle to cycle, consists in adjusting the AVD automatically to maximize the number of heart cycles having a fusion rate included in the target area. It is likely that the degree of fusion varies but little when the adrenergic conditions of the patient are stable, and to preserve the battery of the device, it is advantageous to measure the fusion rate only every C cycles ($1 \leq C \leq 60$ for example). The frequency (C) for evaluating the fusion rate can be reduced (C can be changed from 8 to 1 for example) on detecting an effort and an acceleration of the patient's heart rate, or when the fusion rate between two measurements is very variable.

The decision to change the AVD to maintain the degree of fusion around the target value may be taken from cycle to cycle, or else according to a majority criterion of X cycles over Y (e.g. 6 cycles over 8).

Essentially, after measuring the degree of fusion of the current cycle, the device evaluates the difference between the measured value and the target value. If this difference is in the direction of capture (to the right of the histogram of FIG. 14), the AVD should be increased for the next cycle; conversely, for a variation towards the spontaneous rhythm (to the left of the histogram of FIG. 14) the AVD should be reduced. The variation increment of the AVD can be fixed (1 or 2 predetermined steps), or variable depending on the difference between the measured current fusion rate and the target fusion rate.

If the AVD is modified cycle to cycle according to the degree of fusion of the previous cycle, the device then adapts automatically and quickly to the patient's heart rate and adrenergic state.

The FIG. 15 is an example of a flowchart implementing this manner of proceeding.

The step 200 corresponds to the application of a current AVD value to a cardiac cycle. The degree of fusion of this cycle is measured (block 202), then it is compared with predetermined limit values, for example 95% (in spontaneous rhythm) at the upper limit and 30% (in spontaneous rhythm) at the lower limit.

If this condition is satisfied, then it should be checked whether or not the degree of fusion measured is included within the target range (block 206), namely between 10 and 30% of capture in the example described above. If so, no specific action is taken (return to block 200). If not, the AVD should be modified to bring back the degree of fusion within the target range.

The AVD is then, as the case may be, incremented or decremented (block 208) as explained above.

Before applying the modified value of the AVD, one must check that it remains within the allowable maximum and minimum limits $AVD_{max}$ and $AVD_{min}$ (block 210).

If the upper limit $AVD_{max}$ is reached (block 212), this very likely results from the occurrence of an atrioventricular block, requiring the operating mode of the device (block 214) to be modified, for example to trigger a forced pacing of the right ventricle. It should be noted that this technique makes it possible, by continuous monitoring of the degree of fusion, to identify the occurrence of atrioventricular blocks without the need to monitor the PR or AR interval, thus preventing a risk of insufficient pacing of the patient.

If the lower limit $AVD_{min}$ is reached (block 216), the AVD is not reduced, but limited to this minimum value (block 218). It should be noted that this limit $AVD_{min}$ can be a variable limit, in particular as a function of the patient's activity, for example $AVD_{min}=65$ ms at rest and $AVD_{min}=32$ ms during exercise.

In addition, if, as detected in block 204, the degree of fusion of a majority of cycles within for example the last hour (or half-hour, or any other time interval) falls outside the threshold limits, a counter is incremented (block 220) and periodically tested (block 202). If it is found that a large number of cycles are outside the target area, the pacing mode is probably not appropriate, and another operating mode is chosen (block 214), for example a full biventricular capture.

Figure 16:
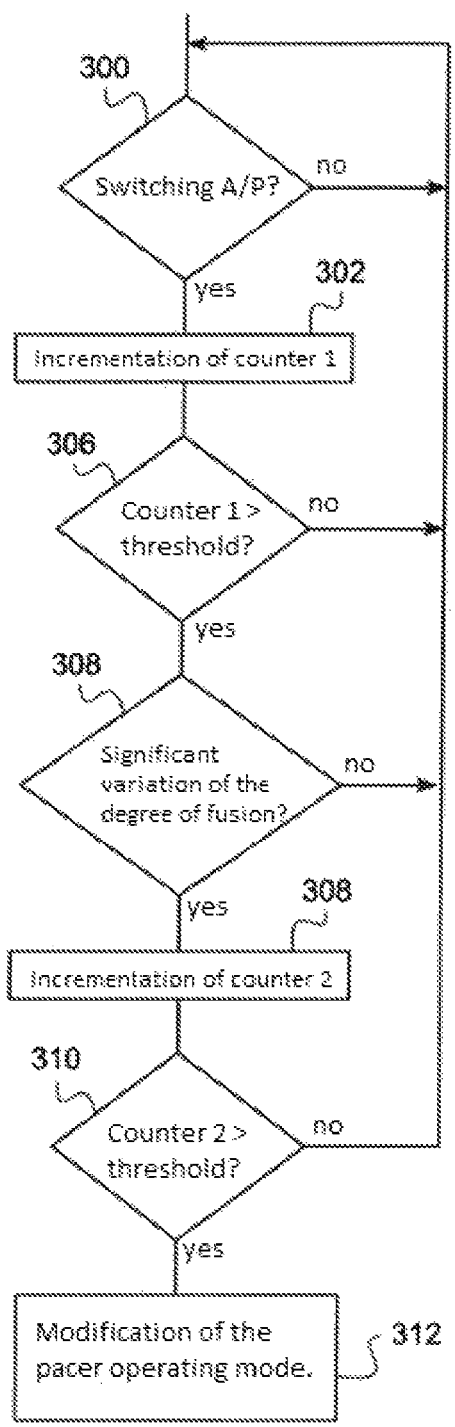
FIG. 16 is a flowchart explaining a complementary control, implemented in case of multiple switching between stimulated mode and spontaneous mode at the atrium.

FIG. 16 is a flowchart explaining a complementary control, implemented in case of multiple switching between stimulated mode and spontaneous mode at the atrium.

As discussed above with reference in particular to FIGS. 11 and 12, in case of transition from a spontaneous atrial rhythm (events P) to a cycle with pacing of the atrium (event A), or vice versa, the device applies to the current AVD a previously determined offset or shift during the creation of the references (as described with reference to FIG. 10), in order to maintain a comparable degree of fusion between the cycles in spontaneous rhythm and stimulated rhythm. However, if the atrial pacing frequency is close to the patient's sinus rate, then it may happen that the device switches repeatedly between mode with pacing of the atrium and mode with spontaneous contraction of the atrium. It can then be considered that for most cycles, a fusion between sinus rhythm and atrial pacing is obtained, and therefore that the offset is not adequate and produces an AVD which is too long, which prioritizes the spontaneous depolarization of the ventricle.

Thus, as illustrated in FIG. 16, at each detected A/P switching (block 300), a first counter (block 302) is incremented and if the value of this counter exceeds a predetermined threshold (block 304), for example ten switching operations during the last minute, the variation of the degree of fusion (block 306) between consecutive cycles is evaluated:
  if this variation is less than a given tolerance, for example 10%, then the variation is considered as not being significant;
  in the opposite case, a counter is incremented each time this variation changes sign (block 308).

If the counter exceeds a given threshold (block 310), for example ten significant variations in the last minute, then it is considered that the degree of fusion is too unstable. An action is then undertaken (block 312), for example:
  no longer applying the offset during the next changes from spontaneous atrial rhythm to a stimulated atrial rhythm;
  or automatically reprogramming the atrial pacing frequency: as appropriate, by lowering this frequency to prioritize the spontaneous rhythm of the patient, or by accelerating this frequency to avoid unnecessary switching due to too close proximity to the sinus frequency.

Figure 17:
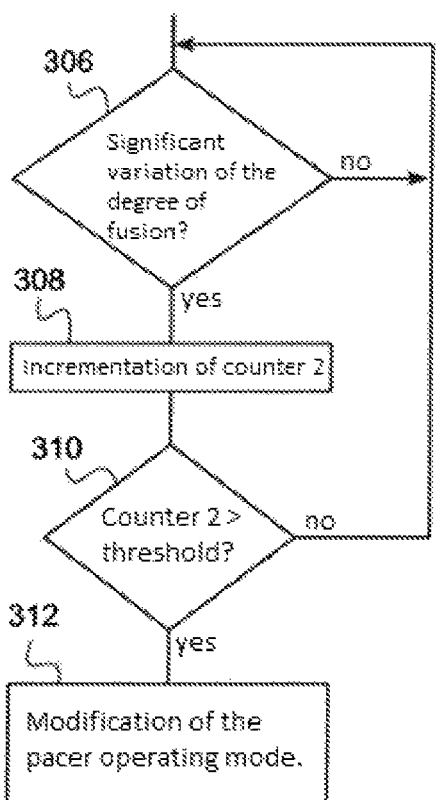
FIG. 17 is a flowchart explaining another complementary control, implemented in case of instability detected at PR or AR intervals.

FIG. 17 is a flowchart explaining another complementary control, implemented in case of instability detected in the PR or AR intervals. FIG. 10 described how to develop the two references, Reference #1 in capture and Reference #2 in spontaneous rhythm. When Reference #2 is developed with a dummy AVD (as shown in FIG. 11), the resulting references correspond to a specific PR interval. But if the PR interval is unstable, for the same pacing parameters, the degree of fusion will not be the same from one cycle to another.

It can therefore be interesting to highlight the instability of the PR or AR interval, without modifying the current parameters of pacing, nor inhibiting the pacing.

As in the case of FIG. 16, changes in capture percentage between consecutive cycles can be monitored (steps 306 and 310 of FIG. 17, identical to the same steps described above with respect to FIG. 16).

When the degree of fusion becomes too unstable (block 310), then it is advisable (block 312):

to switch to another mode of pacing, for example to full biventricular capture;

to maintain pacing of the sole left ventricle as long as the degree of fusion remains within the authorized limits. In the latter case, it may be preferable to use a single reference in spontaneous rhythm (Reference #2), centered on a characteristic point of the signal.

The invention claimed is:

1. An active implantable medical device of the cardiac resynchronizer type, comprising:

a pulse generator comprising a memory having instructions stored thereon and a processor configured to execute the instructions to produce pacing pulses intended to be delivered to at least a left ventricle of a patient carrying the active implantable medical device;

at least one detection electrode, the pulse generator configured to detect atrial and ventricular events via signals received from the at least one detection electrode; and at least one stimulation electrode;

wherein the processor is further configured by the instructions to:

apply an atrioventricular delay (AVD) between a sensed or stimulated atrial event and a delivery of a ventricular pacing pulse;

quantify a degree of fusion between the delivery of a pacing pulse to a cavity, left or right, and a spontaneous contraction of another cavity which is opposite, respectively right or left, and calculate a fusion rate value between two extreme values respectively corresponding to a full capture situation and to a spontaneous depolarization situation of said cavity; and modify a value of the AVD applied to the delivery of said ventricular pacing pulse, as a function of a comparison made between i) a current value of the fusion rate calculated by processor, and ii) a target value of the fusion rate.

2. The device of claim 1, wherein the processor is further configured to quantify a degree of fusion between the delivery of a pacing pulse to the left ventricle and a spontaneous contraction of the right ventricle, and calculate a fusion rate value comprised between two extreme values respectively corresponding to a full capture situation and a situation of spontaneous depolarization of the left ventricle.

3. The device of claim 1, wherein:

the at least one detection electrode is configured to collect, during the same cardiac cycle, concurrently on different respective paths, at least two different endocardial electrogram signals, EGM, and to derive at least two distinct temporal components (Vbip, Vuni); and the processor is further configured to analyze a current cycle by:

combining the at least two distinct temporal components (Vbip, Vuni) in at least one parametric 2D characteristic (VGM) representative of said cardiac cycle, from variations of one of the temporal components as a function of the other; and comparing the 2D characteristic of the current cycle with at least one reference 2D characteristic obtained previously and stored by the device.

4. The device of claim 1, wherein the processor is configured to calculate said value of fusion rate over a given number C of cardiac cycles, $C \geq 1$.

5. The device of claim 4, wherein said given number C of cardiac cycles is a variable number, based on a level of activity of the patient.

6. The device of claim 1, wherein the processor is further configured to:

increment the AVD by at least one step when the current value of the fusion rate has moved with respect to the preceding cycle(s) towards a closer match with said full capture situation, and decrement the AVD by at least one step when the current value of the fusion rate has moved with respect to the preceding cycle(s) towards a closer match with said situation of spontaneous contraction.

7. The device of claim 6, wherein said incrementation/decrementation is an incrementation/decrementation of a variable number of steps, said variable number of steps being a function of a difference between the current value and the target value of the fusion rate.

8. The device of claim 1, wherein the processor is further configured to compare the determined AVD value with an upper limit threshold (AVDmax) and selectively modify an operating mode of the active implantable medical device when crossing said upper limit threshold.

9. The device of claim 1, wherein the processor is further configured to limit said modified AVD value to a minimum floor value ($AVD_{min}$).

10. The device of claim 1, wherein the processor is further configured to:

selectively switch the pulse generator between a mode with atrial pacing (A) and a mode without atrial pacing (P);

detect and count, in a first counter (Counter 1), of the switching operations between modes with and without atrial pacing;

detect and count, in a second counter (Counter 2), of the occurrences where a variation of the current value of the fusion rate between consecutive cycles exceeds a predetermined threshold; and selectively modify the operating mode of the device should predetermined respective counting values be exceeded by the first and the second counter.

11. The device of claim 1, wherein the processor is further configured to:

selectively switch the pulse generator between a mode with atrial pacing (A) and a mode without atrial pacing (P);

detect and count, in a first counter (Counter 1), of the switching operations between modes with and without atrial pacing;

detect and count, in a second counter (Counter 2), of the occurrences where a variation of the current value of the fusion rate between consecutive cycles exceeds a predetermined threshold; and selectively modify the operating mode of the device in the event of the first counter exceeding a first predetermined counting value, while the second counter remains below a second predetermined counting value, and vice versa.

* * * * *